(12) United States Patent
Richter et al.

(10) Patent No.: US 10,845,274 B2
(45) Date of Patent: Nov. 24, 2020

(54) DEVICE HAVING A MICRO FLUID ACTUATOR

(71) Applicant: Fraunhofer-Gesellschaft zur Foerderung der angewandten Forschung e.V., Munich (DE)

(72) Inventors: Martin Richter, Munich (DE); Christian Wald, Munich (DE); Yuecel Congar, Buchloe (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 145 days.

(21) Appl. No.: 16/239,991

(22) Filed: Jan. 4, 2019

(65) Prior Publication Data
US 2019/0154551 A1 May 23, 2019

Related U.S. Application Data

(63) Continuation of application No. PCT/EP2016/065694, filed on Jul. 4, 2016.

(51) Int. Cl.
*G01N 1/00* (2006.01)
*G01N 1/22* (2006.01)
(Continued)

(52) U.S. Cl.
CPC ......... *G01N 1/2273* (2013.01); *F04B 43/043* (2013.01); *F04B 43/046* (2013.01);
(Continued)

(58) Field of Classification Search
CPC .. G01N 1/2273; G01N 1/2205; F04B 43/043; F04B 43/046; F04B 45/047
See application file for complete search history.

(56) References Cited

U.S. PATENT DOCUMENTS 6,432,721 B1 * 8/2002 Zook ................. G01N 1/24
422/82
6,758,107 B2 * 7/2004 Cabuz ................. F04B 43/043
417/320

(Continued)

FOREIGN PATENT DOCUMENTS

EP 2733484 A1 5/2014
JP 2013522512 A 6/2013
(Continued)

*Primary Examiner* — Jamel E Williams
(74) *Attorney, Agent, or Firm* — Perkins Coie LLP; Michael A. Glenn

(57) ABSTRACT

The invention relates to a device having an opening defining a fluid connection between a fluid channel in the device and ambient air, a sensor coupled to the fluid channel, configured to sense at least one component of the ambient air, and a micro fluid actuator connected downstream of the sensor, configured, in the suction stroke, to suck in fluid through the fluid channel and to transport the same towards the sensor, and, in the pressure stroke, to transport the sucked-in fluid through said fluid channel back towards the opening. According to the invention, the sensor is arranged spaced apart from the opening, and the volume of the fluid channel between the sensor and the opening is equal to or smaller than the stroke volume which the micro fluid actuator may convey with a single suction stroke.

17 Claims, 6 Drawing Sheets

(51) Int. Cl.
*F04B 43/04* (2006.01)
*F04B 45/047* (2006.01)
*G01N 33/00* (2006.01)
*F04B 53/20* (2006.01)

(52) U.S. Cl.
CPC ............ *F04B 45/047* (2013.01); *F04B 53/20* (2013.01); *G01N 1/2205* (2013.01); *G01N 33/0009* (2013.01); *G01N 33/0014* (2013.01)

(56) References Cited

U.S. PATENT DOCUMENTS

| | | | |
|---|---|---|---|
| 6,889,567 B2 * | 5/2005 | Cabuz | F04B 43/043 |
| | | | 417/413.1 |
| 7,197,949 B2 * | 4/2007 | Zook | G01N 1/24 |
| | | | 422/50 |
| 10,518,262 B2 * | 12/2019 | Sprague | B01L 3/50273 |
| 2005/0229675 A1 | 10/2005 | Haupt et al. | |
| 2013/0055889 A1 * | 3/2013 | Herz | F16K 99/0048 |
| | | | 92/96 |
| 2014/0069420 A1 * | 3/2014 | Richter | A61M 5/0065 |
| | | | 128/200.21 |
| 2014/0134053 A1 | 5/2014 | Mayer et al. | |

FOREIGN PATENT DOCUMENTS

| | | |
|---|---|---|
| WO | 0130497 A2 | 5/2001 |
| WO | 0194920 A2 | 12/2001 |
| WO | 2015104221 A1 | 7/2015 |

\* cited by examiner

DEVICE HAVING A MICRO FLUID ACTUATOR

CROSS-REFERENCE TO RELATED APPLICATIONS

This application is a continuation of copending International Application No. PCT/EP2016/065694, filed Jul. 4, 2016, which is incorporated herein by reference in its entirety.

The invention relates to a device having the features of claim 1.

BACKGROUND OF THE INVENTION

Nowadays, more and more sensors are used. Many of these sensors measure environmental parameters such as $CO_2$, moisture, temperature or smoke. However, these sensors naturally do not measure the parameters of the room but the parameters within the respective device into which they are integrated. Then, an attempt is made to approximately extrapolate the parameters of the room air from the measuring signal of the sensor by means of complicated algorithms, which only partially succeeds.

Detecting gases such as CO, $N_2O$ or VOC as well as water contents and the gas composition in our surroundings is in the interest of many people.

In addition, most people would like to instantly sense air polluting gases, fine dust and allergenic particles such as pollen at their location or receive early warnings of allergenic substances and hazardous gases. Moreover, detecting odors such as breath alcohol, bad breath and many other odors is of interest.

A further field of application of the measurement of parameters of the surroundings is the so-called context awareness of mobile devices. In this case, the device itself reacts to its direct surroundings by switching on or off or by adapting functions such as acoustic signal tones or vibrating alerts and transmission functions or by switching off power consumers for saving battery life. Examples for this are the recognition of interior and exterior spaces or aircrafts, the presence of other people or the carrying style, e.g., away from the body in a purse or in briefcase, or close to the body in the pocket of a shirt or of trousers.

Sensors are available for many of the applications mentioned. Although many of the available sensors (e.g., for humidity, volatile organic compounds VOC, CO or NO) or of the sensors based on metalorganic principles, optical principles or resonance principles comprise form factors and an appropriate cost efficiency for the utilization with portable devices, the commercial use is only possible in a limited extent, since, with respect to the sensor principles, the gas, the odor or the fine dust may not be transported quickly and reliably to the sensor in a portable device in all of them.

However, this is necessary in order to provide the user with a meaningful and fast measurement result. Reliable data for gas measurements may provide meaningful gas overviews of the surroundings, e.g., air pollution along streets or in large cities, or pollen maps for people suffering from allergies.

In some cases, sensors are installed in bulky, stand-alone devices. In some cases, mouth pieces have to be used with these devices, which many people do not like. An additional problem is that stand-alone devices with sensors require display capabilities and computing capabilities, which incurs additional costs.

Such a specialized portable gas measuring device is known from WO 2015/104221 A1. The Reference relates to a sensor unit for a gas measuring device for detecting a gas. The transportable gas measuring device serves to monitor gases and vapors, in particular toxic gases in industrial environments. In general, it is about the change in a physical-chemical property of the receptor, which interacts with analyte molecules at the molecular level. In this connection, WO 2015/104221 A1 describes a combination of a pressure-tight measuring channel, a gas inlet, a gas outlet, a pump unit for evacuation, a gas sensor, a heating unit for the gas sensor and a sensor unit with a regeneration mode and a measuring mode.

As mentioned at the outset, the gas measuring device known from WO 2015/104221 A1 is a specialized apparatus exclusively intended for measuring gases in the ambient air. Such apparatuses provide good and reliable measurement results. However, such apparatuses require a certain amount of time during which a gas sensor technology calibrates itself to provide a sufficiently reliable result. Such known devices are therefore not immediately ready for use, especially in cases in which the conditions of the surroundings rapidly change. For example, this is the case when the device is moved from an outside area to an interior area such as a living room. In this case, known apparatuses require a certain amount of time to "acclimatize", so to speak, which may be up to several minutes.

However, fast response times of the gas sensors are desirable for many applications of portable electronic devices, e.g., in the case of a rapid recognition of people by means of gas sensors, in the case of fire detection sensors or in order to sense when a person is entering a building. When taking this knowledge into account, the manufacturer of gas measuring devices would have to mount sensors directly onto the housing surface in order to obtain a rapid signal. However, this is uneconomical or unfavorable for several reasons.

On the one hand, arranging the sensor on one of the circuit boards in the housing increases the assembly requirements and, inevitable, the associated assembly costs. In addition, if mounted directly onto the housing surface, there is the risk of damage to the sensor by external influences. On the other hand, if the sensor is installed on the outside of the gas measuring device, the housing may no longer be smooth. Moreover, when many gas sensors and other components (e.g., circuit boards, displays, etc.) are to be mounted close to the air inlet of the gas measuring device, there may not be enough available space.

A humidity sensor was already used as a standard in smartphones. However, this sensor had long response times in the range of several minutes. The sensor was located in the housing of the smartphone. The smartphone housing comprised a housing opening through which the air was diffused to the sensor. However, diffusion as a transport mechanism between the housing opening and the sensor was very slow.

Currently, sensor developers work on shortening the response time. One solution proposes positioning the sensor as close as possible to the opening in order to shorten the diffusion path and, thus, the time required for diffusion.

A further solution proposes predicting from the initial increase of the sensor signal the final value by means of software. Thus, an initial sensor value is sufficient in order to extrapolate the further progress and, thus, to save time.

However, both solutions have technical limits. Thus, realizing a sensor response time of less than 20-30 seconds is hardly possible.

Currently, besides humidity sensors, there is a trend to integrate further sensors measuring air parameters into a mobile radio device and into other wearable devices (wearables, watches, etc.).

In all these sensors, the response time is a critical parameter which has not been sufficiently solved to date. For example, mobile communications manufacturers require the output of a sensor value already within one to two seconds after the user has requested the value. However, this requirement may not be sufficiently solved without a micro actuator, or a micro fluid actuator, actively pumping the air sample (i.e., by means of convection) to the sensor.

Several mobile devices have already been presented which have a micro pump in which a silicon micro membrane pump is responsible for supplying air to the sensor. With this, fast response times may be realized. However, this technology has some difficulties.

For example, the micro pumps used in this case are unidirectional. That is, after reaching the sensor, the medium to be pumped has to leave the mobile device in a different way. Either the air is pumped into the mobile device (which has other disadvantages) or a second housing opening is required in order to transport the air back out of the device.

Solutions are also known for this, in the form of bidirectional micro pumps. Bidirectional micro pumps (e.g., a micro peristaltic pump having three piezo actuators, developed by Fraunhofer EMFT) suck in air in a suction stroke and pump out said air in an outlet stroke. However, bidirectional micro pumps are substantially larger than unidirectional micro pumps and, thus, manufacturing the same is more expensive.

Additionally, all mechanical micro pumps and valves comprise movable parts. If particles are sucked in, these may jam in the micro valves, which leads to a performance decay of the micro pump or to the failure of the micro pump.

SUMMARY

According to an embodiment, a device may have: a housing with a housing opening defining a fluid connection between a fluid channel in the device and ambient air, a sensor coupled to the fluid channel and disposed in the housing, configured to sense at least one component of the ambient air, a micro fluid actuator arranged downstream of the sensor and disposed in the housing, configured, in the suction stroke, to suck in fluid through the fluid channel and to transport the same towards the sensor, and, in the pressure stroke, to transport the sucked-in fluid through said fluid channel back towards the housing opening, the sensor being arranged spaced apart from the housing opening, and the volume of the fluid channel between the sensor and the housing opening being equal to or smaller than the stroke volume which the micro fluid actuator may convey with a single suction stroke, wherein the stroke volume of the micro fluid actuator is at least 2.5 times larger than the volume of a fluid channel portion between the sensor and the housing opening, and wherein the micro fluid actuator is a membrane actuator having a carrier and a deflectable membrane arranged at the same, and the membrane is mechanically biased so that the membrane is spaced apart from the carrier in an unoperated idle position and, upon operation, moves towards the carrier.

The device according to the invention comprises, among others, an opening defining a fluid connection between a fluid channel in the device and ambient air. Preferably, the opening is a housing opening, i.e., an opening in the housing of the device. The opening connects the interior of the device with the surroundings, i.e., a fluid, in particular air, may flow into this device from the outside through said opening. In particular, the opening connects the surroundings with the fluid channel arranged in the interior of the device. For example, the fluid channel may be a thin tube, a hose or the like. The fluid channel may be rigid; however, it may preferably flexible. The device according to the invention further comprises a sensor coupled to the fluid channel, configured to sense at least one component of the ambient air. The sensor is fluidically coupled to the fluid channel, i.e., the sensor may be arranged in or at the fluid channel, provided that the fluid flowing though the fluid channel at least partially flows to the sensor, or through the sensor. Furthermore, the device according to the invention comprises a micro fluid actuator arranged downstream of the sensor. Said micro fluid actuator is configured to suck in, in the suction stroke, a fluid through the fluid channel and to transport the same towards the sensor, and to transport, in the pressure stroke, the sucked-in fluid through said fluid channel back towards the opening. The micro fluid actuator is a means for sucking in (suction stroke) and ejecting (pressure stroke) of fluid. In doing so, the micro fluid actuator sucks in a fluid (e.g., ambient air) into the fluid channel through the opening from the outside. The fluid flowing in flows to the sensor coupled to the fluid channel. After sucking in, the micro fluid actuator ejects the sucked-in fluid back out, again through the fluid channel, however, in the opposite direction so that the sucked-in fluid is ejected back out into the surroundings through the opening. In other words, the micro fluid actuator pushes a fluid volume located in the fluid channel back and forth. According to the invention, the volume of the fluid channel (or the volume of the fluid located in the fluid channel) between the sensor and the opening is as large as or smaller than the stroke volume which the micro fluid actuator may convey in a single suction stroke. That is, the micro fluid actuator may move in a single suction stroke the required amount of a fluid volume in the fluid channel so that the fluid to be sucked in through the opening from the outside travels the entire length from the opening to the sensor.

It is conceivable that the fluid channel extends between the opening and the micro fluid actuator, and that the fluid channel, the sensor coupled to the fluid channel, and the micro fluid actuator together form a fluid-tight arrangement which is sealed against the interior of the mobile device (1). This favors the accuracy in displacing the small fluid volume (in the range of micro liters) located in the fluid channel. Essentially, the fluid-tight arrangement should be sealed against the remaining mobile device so that, e.g., ambient air sucked in through the opening of the mobile device does not mix with the device air located in the interior of the mobile device. Certain small gas leakage rates would be acceptable as long as they do not falsify the result of the sensor system.

It is conceivable that the stroke volume of the micro fluid actuator is at least 2.5 times, or preferably at least 10 times, larger than the volume of the fluid channel between the sensor and the opening. In this way, it may be ensured that, upon sucking in the ambient air by means of the micro fluid actuator, a sufficient amount of fluid flows through the fluid channel and reaches the sensor arranged in the fluid channel.

According to an embodiment, the mobile device is a mobile telephone and the opening provided in the mobile telephone is a microphone opening. Thus, providing an additional device opening is not necessary since the microphone opening is already present in a mobile telephone.

According to a further embodiment, the sensor may be configured to sense at least one ambient air component from the group of carbon monoxide (CO), carbon dioxide ($CO_2$), nitrogen (N), nitrous oxide ($N_2O$), volatile organic compounds (VOC), humidity and fine dust. That is, the sensor may, for example, sense if such an ambient air component is present, and the sensor may also determine the concentration of this ambient air component.

According to a conceivable embodiment, the micro fluid actuator may be a membrane actuator having a deflectable membrane, and the membrane may be operable in a piezoelectric or electromagnetic or electrostatic manner or by means of electroactive polymer actuators or by means of an element comprising a shape memory alloy. A fluid is conveyed by means of stroke movements of the membrane. The membrane may be deflected from its idle position by means of said operating means in order to execute a stroke movement (suction stroke and/or pressure stroke) and to convey the fluid through the fluid channel. A membrane actuator structured in such a simple manner is advantageous compared to, e.g., (micro) membrane pumps since pumps comprise an inlet and an outlet which, in turn, have to be opened or closed with inlet valves and outlet valves, respectively, at the right moment. That is, pumps generally comprise a fluid channel on the inlet side as well as a fluid channel on the outlet side. In contrast, the membrane actuator according to the invention solely comprises a single fluid channel through which the fluid flows in in the suction stroke and through which the fluid flows out in the pressure stroke.

It is conceivable that the device is a mobile telephone having a vibrating alert motor and that the micro fluid actuator is a membrane actuator having a deflectable membrane, the membrane being operable by means of the vibrating alert motor. Thus, the vibrating alert motor already present may be used for operating the membrane, i.e., separate operation means may be omitted. In turn, this saves construction space, which is an important criterion in today's devices, in particular in mobile devices.

According to an embodiment, the micro fluid actuator may be a membrane actuator having a deflectable double membrane. With this, mechanical stress acting upon the membrane when operating the same may be kept lower as compared to a single membrane.

It is conceivable that the micro fluid actuator is a membrane actuator having a carrier and a deflectable membrane arranged at the same, and that the membrane is mechanically biased so that the membrane, in an unoperated idle position, is spaced apart from the carrier and, upon operation, moves towards the carrier. For example, the membrane may be a biased metal membrane such as a stainless steel membrane. Due to the bias, the membrane is arched so that, in its idle position, it is spaced apart from the carrier. The cavity formed between the carrier and the biased membrane may, e.g., determine the stroke volume of the micro fluid actuator. In the case of an exemplary electrical operation of the membrane, the membrane may be operated by applying a (e.g., positive) electrical voltage so that, consequently, the membrane moves towards the carrier. In this case, the membrane executes a pressure stroke and the micro fluid actuator conveys a fluid which, in this case, moves away from the micro fluid actuator. If the electrical voltage is no longer applied (or, e.g., a negative electrical voltage is applied), the membrane returns to its pre-biased idle position, i.e., it moves away from the carrier. Accordingly, a negative pressure sucking in the fluid is formed in the fluid channel. That is, the micro fluid actuator executes a suction stroke and conveys the fluid which, in this case, moves towards the micro fluid actuator.

It is conceivable that the micro fluid actuator is a membrane actuator having a carrier and a deflectable membrane arranged at the same, and that the membrane including the carrier comprises a height of 0.50 mm or less. Such a height is advantageous in order to integrate the micro fluid actuator into a housing, in particular, of a mobile device.

According to an embodiment, the device may comprise two or more sensors arranged successively in series in the flow direction. An arrangement in series means that the individual sensors may be arranged in the fluid channel in a spatially successive manner in the flow direction so that a fluid flowing through the fluid channel flows through the respective sensors in a temporally successive manner. The individual sensors may each measure other parameters, or components, of the sucked-in fluid.

According to a further conceivable embodiment, the device may comprise two or more sensors arranged in parallel in the flow direction. A parallel connection of individual sensors means that the fluid channel splits, and that at least one sensor is arranged in each branch. In this case, a fluid flowing through the fluid channel flows through each sensor at approximately the same time. In the parallel connection, it is practical if the flow resistances of all sensors are approximately the same. A parallel connection of sensors and a connection of sensors in series may also be combined so that several sensors are connected in series in a parallel branch.

In this case, it is conceivable that the device comprises two or more micro fluid actuators, each micro fluid actuator being in fluid connection with a respective sensor. Irrespective of the fact that the several sensors are connected to each other in series or in parallel, preferably, each individual sensor has associated therewith its own micro fluid actuator. Thus, each sensor may be operated independently. This increases the operation reliability, e.g., upon failure of a micro fluid actuator, so that the other micro fluid actuators which are still operable may continue to operate.

It is conceivable that an air-permeable filter element is arranged between the opening and the sensor, configured to collect liquid condensed in the sucked-in fluid. For example, this may be an activated carbon filter, a hydrophobic filter, a hydrostatically charged filter or a Teflon filter. The air-permeable filter element may be an air-permeable membrane which collects condensed liquid, e.g., a hydrophobic (e.g., Teflon-coated) filter membrane having a small pore size and a large "bubble point" in order to protect the sensor from liquid.

Alternatively or additionally, it is conceivable that an air-permeable filter element is arranged between the sensor and the micro fluid actuator, configured to collect liquid condensed in the sucked-in fluid. For example, this may also be an activated carbon filter, a hydrophobic filter, a hydrostatically charged filter or a Teflon filter. The air-permeable filter element may be an air-permeable membrane which collects condensed liquid, e.g., a hydrophobic (e.g., Teflon-coated) filter membrane having a small pore size and a large "bubble point" in order to protect the sensor from liquid.

According to embodiments, the device is a mobile device. According to conceivable embodiments, the mobile device may be a mobile telephone or a smartphone or a wearable or a mobile computer. Wearables are mobile devices which are wearable at the body, in particular computers, e.g., in the form of watches, headbands and the like. Mobile computers are also known as laptops, notebooks or netbooks.

It is a further advantage of the invention that, with this "single-stroke actuator", the air to be measured may be sucked to the sensor in an extremely fast manner (as compared to micro pumps): if the voltage is applied very quickly (e.g., within one or several milliseconds), the actuator also moves in this time constant. Then, the negative pressure, or positive pressure, which is generated "drives" the fluid into the sensor channel. Solely the viscous friction of the air at the channel or the filter element acts in a "decelerating" manner. By means of a corresponding implementation, it is possible to transport the ambient air to the sensor in less than a second, or in less than 100 milliseconds.

This speed would be hardly realizable with micro membrane pumps: if one wanted to convey a dead volume of, e.g., 5 mm$^3$ within 0.1 seconds, one would require a pump rate of 50 mm$^3$/s or 3 ml/min. However, such conveying rates are only realizable with, e.g., silicon micro pumps if the chip size and, thus, the stroke volume are large. However, these micro pumps would be expensive and uneconomical.

It is known from the piezo technology that a piezo membrane converter should not be driven too quickly in order to not diminish its service life. In this case, it has to be considered that the voltage edge is not quick enough for modes to be excited over the mechanical natural frequency. Otherwise, high mechanical stresses occur and a subcritical crack propagation could be induced which decreases the piezo effect and may also lead to breaks of the piezo ceramics.

The natural resonance depends on the geometry and the elasticity module of the membrane and the piezo. In "normal" micro pumps, the natural frequencies are in the range of 10 . . . 30 kHz. In this idea, the stroke volume has to be large, while the blockage pressure should not be too large. Therefore, the natural frequencies may be significantly lower, down to 1 kHz or less. In order to ensure a long service life, it is necessary to select the rising edge of the drive voltage to be significantly slower, e.g., 10 milliseconds or more. This rising time protects the micro actuator from breakage; however, it is still quick enough for a response time of below one second.

Furthermore, with this micro actuator, other operation modes could be chosen by appropriately modulating the voltage signal. For example, the flow speed with which the gas to be measured flows by the sensor element could simply be varied by the actuator speed. Or, pulsed gas portions could be generated. Or, the gas could be conveyed in a first step to a first sensor, and in a second step to a sensor arranged downstream thereof. Depending on the sensor principle, this may be advantageous.

BRIEF DESCRIPTION OF THE DRAWINGS

Embodiments of the present invention will be detailed subsequently referring to the appended drawings, in which.

DETAILED DESCRIPTION OF THE INVENTION

With reference to the figures, embodiments are described in the following based on mobile devices. In embodiments, the device may be a stationary device such as a sensor node or the like so that the respective discussions also apply for stationary devices. For example, a stationary sensor node may function with a battery in an independent manner and may record sensor data and communicate the same.

Figure 1:
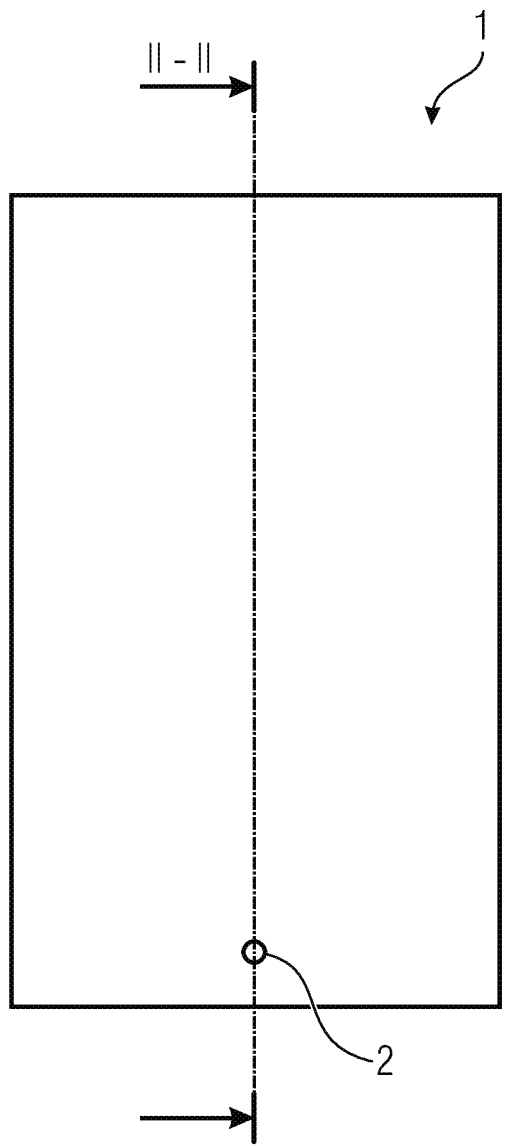
FIG. 1 shows a top view of an embodiment of the mobile device according to the invention.

FIG. 1 shows an embodiment of a mobile device 1 according to the invention having an opening 2. The opening 2 is a housing opening defining a fluid connection between a fluid channel in the mobile device and ambient air.

Figure 2:
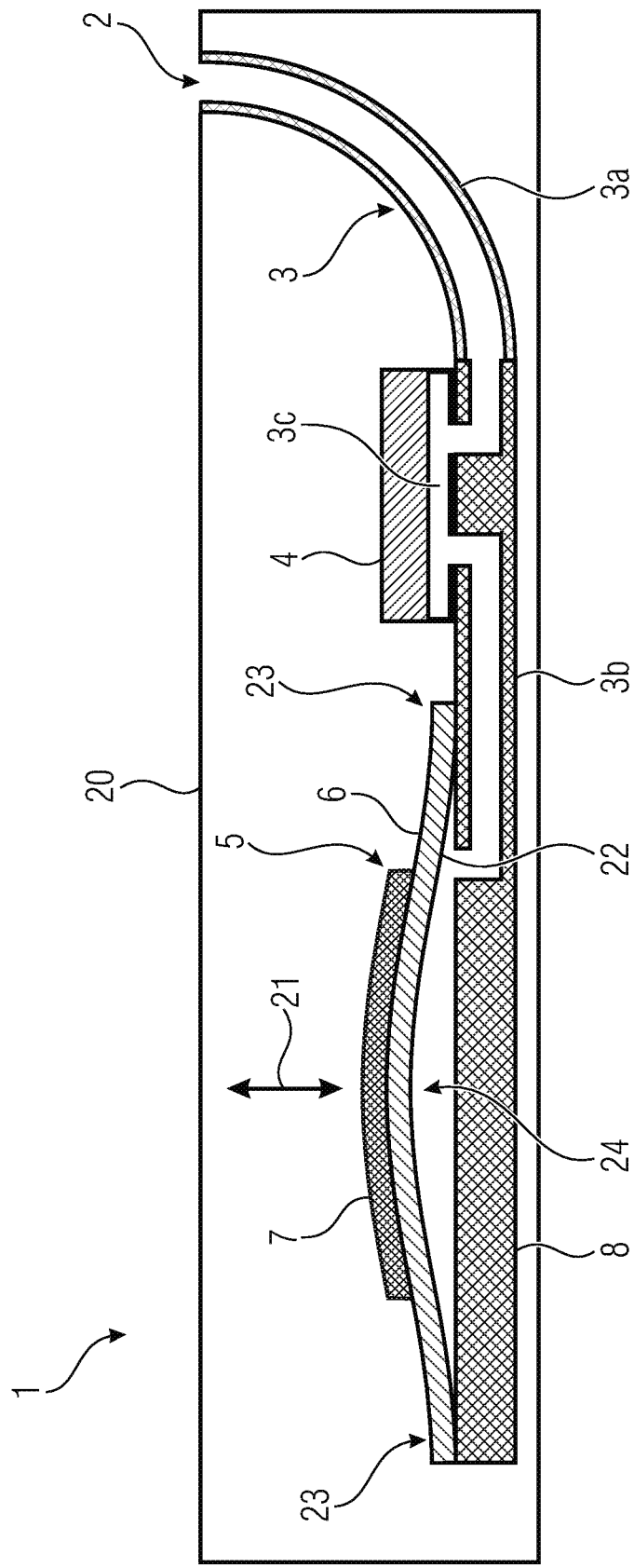
FIG. 2 shows a sectional view of an embodiment of a mobile device according to the invention along the section line II-II shown in FIG. 1.

FIG. 2 is a sectional view through the mobile device 1 along the sectional line II-II shown in FIG. 1. In FIG. 2, the housing 20 of the mobile device 1 can be recognized. The housing 20 comprises the opening 2.

The above-mentioned fluid connection 3 is arranged in the mobile device 1. A sensor 4 is coupled to the fluid channel 3. The sensor 4 is configured to sense at least one component of the ambient air.

Furthermore, a micro fluid actuator 5 is arranged in the mobile device 1. The micro fluid actuator 5 is also coupled to the fluid channel 3. The micro fluid actuator 5 is arranged downstream of the sensor 4 in the fluid channel 3. In other words, the sensor 4 is fluidically coupled to the fluid channel 3 and is arranged between the opening 2 and the micro fluid actuator 5.

Thus, the fluid channel 3 comprises a first portion 3a extending between the opening 2 and the sensor 4, and a second portion 3b extending between the sensor 4 and the micro fluid actuator 5.

The micro fluid actuator 5 is configured to suck in, in the suction stroke, a fluid through the fluid channel 3 and to transport the same towards the sensor 4. Furthermore, the micro fluid actuator 5 is configured to transport, in the pressure stroke, the sucked-in fluid located in the fluid channel 3 through the fluid channel 3 back towards the opening 2.

The sensor 4 is arranged spaced apart from the opening 2. Compared to known solution in which the sensor 4 is placed as close as possible to the opening 2 in order to keep the paths of the fluid flow as short as possible, a spaced-apart arrangement of the sensor 4 according to the invention provides the possibility to arrange the sensor 4 at almost all locations in the mobile device 1. In particular, this is desirable with respect to ever flatter mobile devices 1 as these do not provide unlimited space for installing sensor systems.

According to the invention, the volume of the first portion 3a of the fluid channel 3 between the sensor 4 and the opening 2 is as large as or smaller than the stroke volume which the micro fluid actuator 5 may convey with a single suction stroke.

The fluid channel 3 extends between the opening 2 and the micro fluid actuator 5. Together, the fluid channel 3, the sensor 4 coupled to the fluid channel 3, and the micro fluid actuator 5 form an arrangement which is sealed against the interior of the mobile device (1). That is, the fluid channel 3 as well as the sensor 4 and the micro fluid actuator 5 are embodied in a sealed manner, in particular air-tight.

Figure 3:
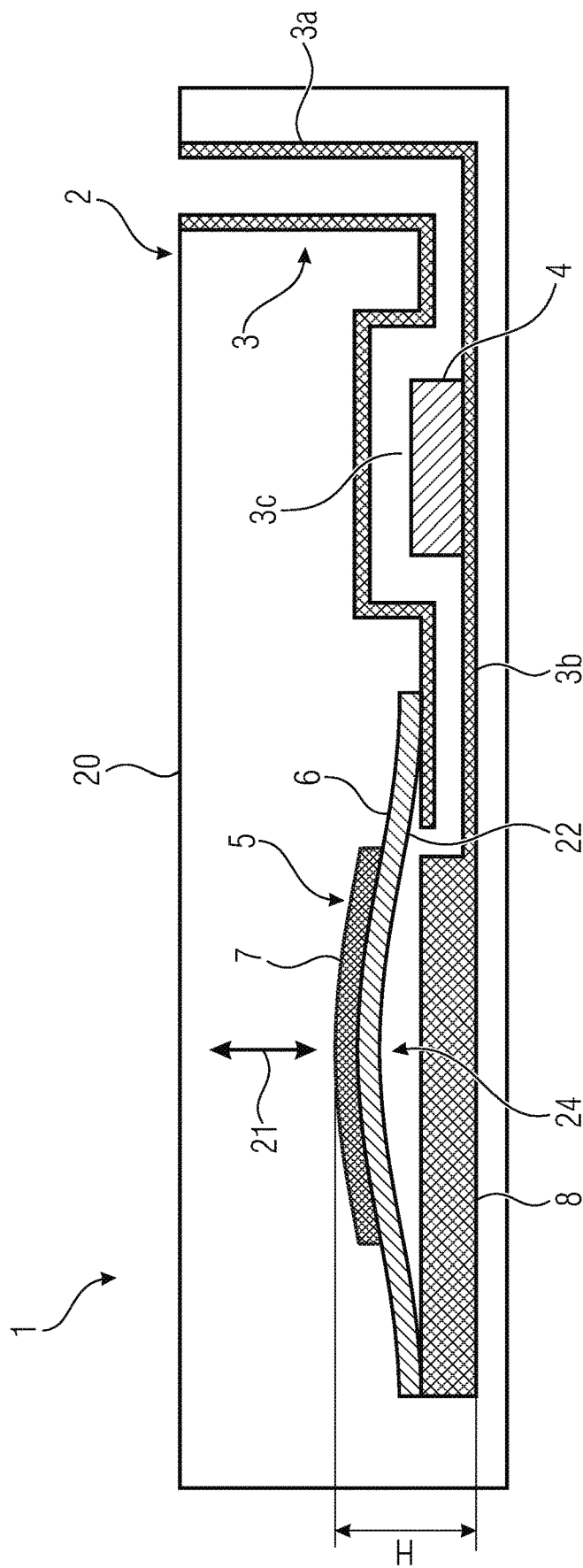
FIG. 3 shows a sectional view of an embodiment of a mobile device according to the invention.

In the embodiments illustrated in FIGS. 2 and 3, the micro fluid actuator 5 is configured as a membrane actuator. The micro fluid actuator 5 comprises a deflectable membrane 6. The membrane 6 may be operated in a piezoelectric, electromagnetic, electrostatic manner by means of electroactive polymer actuators or by means of an element comprising a shape memory alloy.

An operating means 7 configured accordingly is arranged at the membrane 6 for the purpose of deflecting the same. As can be recognized in the figures, the membrane 6 is arranged with one side 22 at a carrier 8. For example, the carrier 8 may be configured as a silicon chip or as a metal body or a polymer body.

In particular, the membrane 6 is arranged at the carrier 8 at the laterally outer portions 23 of the same. In the top view, the membrane 6 may comprise a round or a rectangular shape, in particular a hexagonal shape. The membrane 6 may be attached, or fixed, on the carrier 8 by means of an attaching means, e.g., by means of an appropriate adhesive.

In the embodiments illustrated in the figures, the membrane 6 is arranged on the carrier 8 under a mechanical bias. That is, due to the bias, the membrane 6 comprises a concave arch (directed away from the carrier 8). As a result, a cavity 24 is formed between the carrier 8 and the membrane 6 in the area of this arch. The volume of this cavity 24 essentially determines the stroke volume of the micro fluid actuator 5.

As is indicated by the double arrow 21 in FIGS. 2 and 3, the micro fluid actuator 5 may essentially move in two directions. In an unoperated idle position, the micro fluid actuator 5 is located in the illustrated position in which the membrane 6 is biased and the above-mentioned cavity 24 is configured. Thus, in this idle position, the membrane 6 is spaced apart from the carrier 8.

Now, the operating means 7 may operate the membrane 6. For example, the operating means 7 may be a piezo element which, upon applying a voltage, deflects the membrane 6 downwardly, i.e., towards the carrier 8. Thus, upon operating the membrane 6, the same moves towards the carrier 8 until the membrane 6 contacts the carrier 8 with its bottom side 22.

In doing so, the micro fluid actuator 5 displaces the volume of the fluid located in the cavity 24 at this point in time. Then, this fluid volume is transported through the fluid channel 3 and exits from the opening 2 into the surroundings. Thus, in this case, the micro fluid actuator 5 executed a pressure stroke and the ejected fluid volume substantially corresponds to the stroke volume of the micro fluid actuator 5.

Now, the operating means 7 may move the membrane 6 back in the opposite direction, i.e., in the direction away from the carrier 8. In the case of a biased membrane 6, it is already sufficient if the operating means 7 does no longer apply an operating force to the membrane 6. Then, the membrane 6 returns back to its original initial position due to the mechanical bias.

Hence, in this case, the membrane 6 moves away from the carrier 8 and, thus, again increases the cavity 24 formed between the membrane bottom side 22 and the carrier 8. A negative pressure is formed in the fluid-tight arrangement (micro fluid actuator 5, sensor 4, fluid channel 3) and a fluid is sucked in from the surroundings through the opening 2. Hence, in this case, the micro fluid actuator 5 executes a suction stroke.

The fluid channel 3, i.e., the front portion 3a, the rear portion 3b and the portion 3c circumflowing the sensor 4 of the fluid channel 3 comprise a certain volume. This volume is also referred to as total dead volume.

According to the invention, the stroke volume of the micro fluid actuator 5 is at least as large as the total dead volume. However, it may already be sufficient if the stroke volume of the micro fluid actuator 5 is at least as large as the volume of the front fluid channel portion 3a. Thus, a suction stroke of the micro fluid actuator 5 just conveys a sufficient amount of volume through the front fluid channel portion 3a so that a fluid sucked in at the opening 2 just reaches the sensor 4.

In order to ensure circumflowing the sensor 4 with a sucked-in fluid, embodiments of the invention provide that the stroke volume of the micro fluid actuator 5 is at least 2.5 times larger than the volume of the fluid channel 3 between the sensor 4 and the opening 2, i.e., than the front fluid channel portion 3a.

In the embodiment illustrated in FIG. 2, the sensor 4 is fluidically coupled to the fluid channel 3 by arranging the sensor 4 at the fluid channel 3. In the embodiment illustrated in FIG. 3, the sensor 4 is fluidically coupled to the fluid channel 3 by arranging the sensor 4 not at the fluid channel 3, but in the same.

As can be recognized in FIG. 3, the micro fluid actuator 5 comprises a height H extending between the bottom side of the carrier 8 and the top side of the membrane 6, or of the operating means 7 arranged at the membrane 6. According to advantageous embodiments, the micro fluid actuator 5 comprises a height H of 0.50 mm or less.

Figure 4:
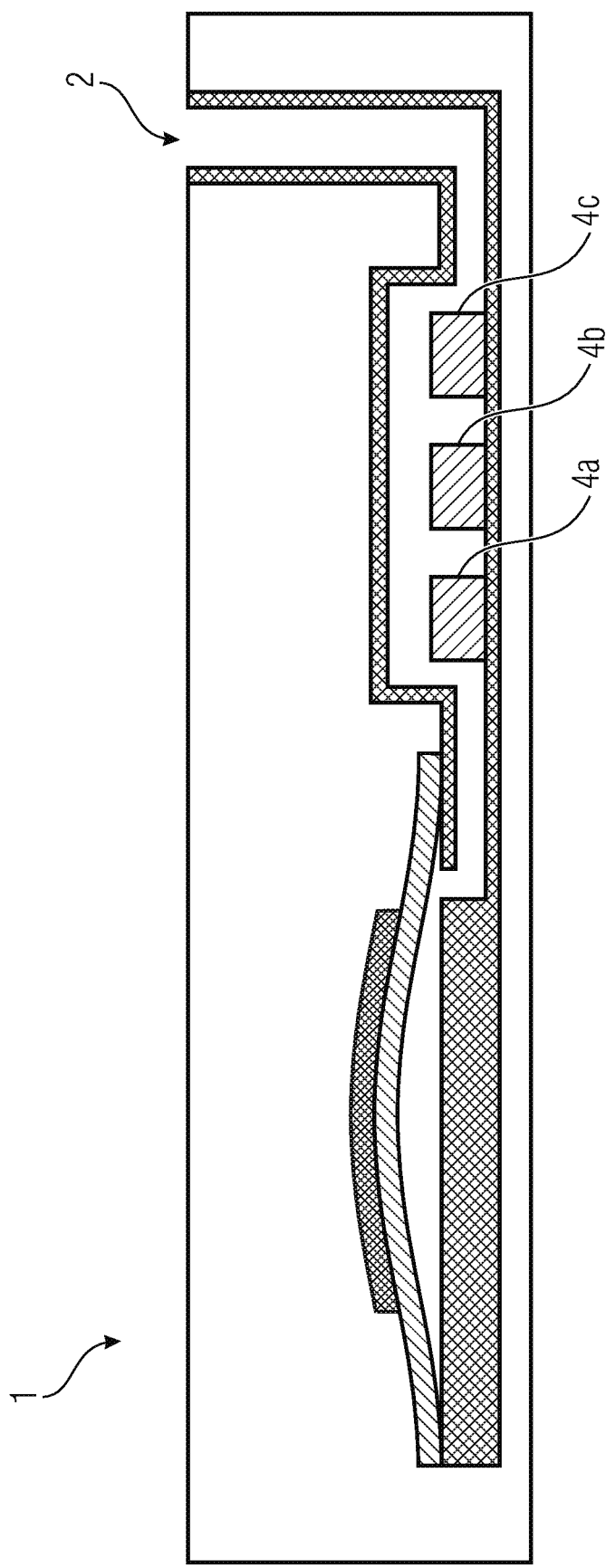
FIG. 4 shows a sectional view of an embodiment of a mobile device according to the invention having a series connection of several sensors.

FIG. 4 shows a further embodiment of a mobile device 1 according to the invention. Here, the mobile device 1 comprises three sensors 4a, 4b, 4c arranged successively in series in the flow direction (both in the suction direction and in the ejection direction).

Figure 5:
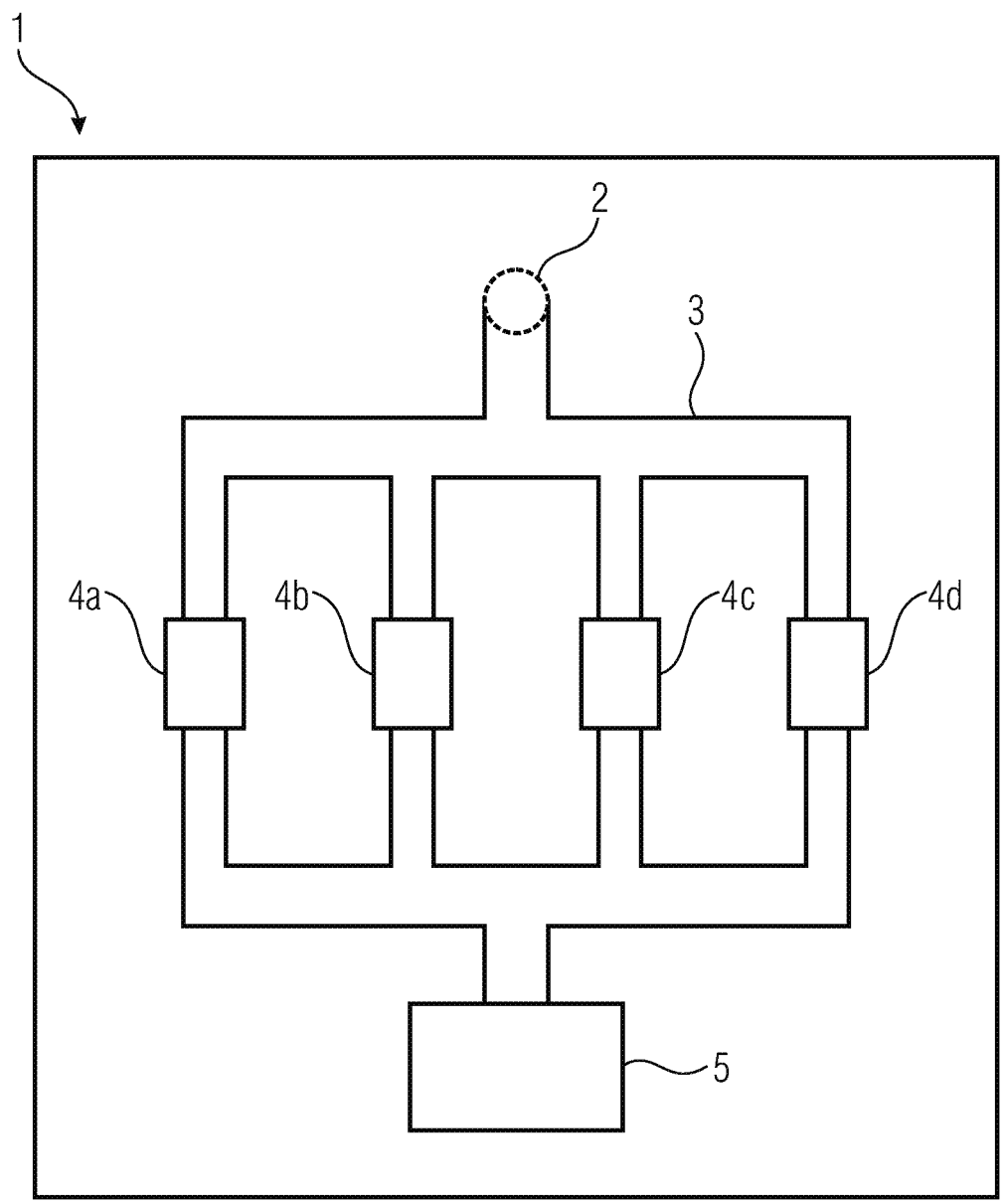
FIG. 5 shows a top view of an embodiment of a mobile device according to the invention having a parallel connection of several sensors.

FIG. 5 shows a further embodiment, wherein the mobile device 1 comprises four sensors 4a, 4b, 4c, 4d, arranged in parallel in the flow direction. In this embodiment, the mobile device 1 comprises a micro fluid actuator 5 configured to supply the parallel connection of several sensors 4a to 4d together with sucked-in ambient air.

Figure 6:
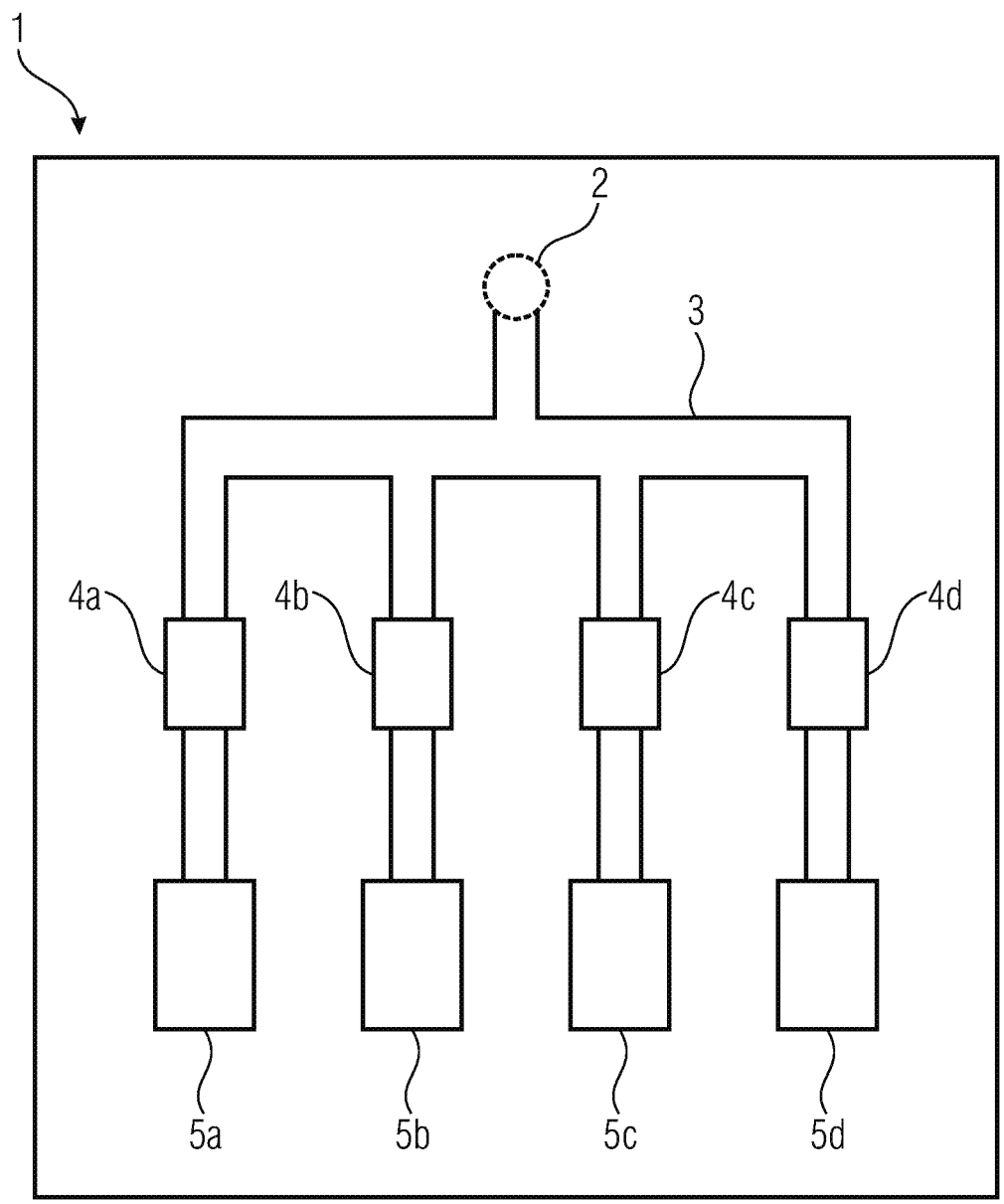
FIG. 6 shows a top view of a further embodiment of a mobile device according to the invention having a parallel connection of several sensors.

FIG. 6 shows a further embodiment, wherein the mobile device 1 comprises four micro fluid actuators 5a, 5b, 5c, 5d as well as four sensors 4a, 4b, 4c, 4d. Here, each micro fluid actuator 5a, 5b, 5c, 5d is in fluid connection with a respective sensor 4a, 4b, 4c, 4d. For example, each of the four sensors 4a to 4d may analyze a certain ambient air parameter. Thus, the sensors 4a to 4d may work in a needs-based manner by separately driving the respectively associated micro fluid actuator 5a to 5d.

After the embodiment of the mobile device 1 according to the invention has been described structurally, the mode of operation is to be explained in the following.

For example, the sensor 4 may be a sensor for measuring carbon monoxide (CO), carbon dioxide ($CO_2$), nitrogen (N), nitrous oxide ($N_2O$) volatile organic compounds (VOC), humidity or fine dust. For this purpose, the sensor 4 has to be circumflowed with ambient air.

For example, the mobile device 1 may be a smartphone having an already existing microphone opening 2. The ambient air may be sucked in through this microphone opening 2. For this purpose, a fluid line 3 is arranged at the microphone opening 2. This fluid line 3 leads to the sensor 4.

Diffusion of the ambient air from the opening 2 to the sensor 4 takes a relatively long time. Therefore, the invention provides the micro fluid actuator 5 which sucks in the ambient air through the opening 2. Thus, the sucked in ambient air flows substantially faster to the sensor 4 which, on the other hand, may generate signals more quickly.

Hence, known solutions functioning with the diffusion principle are replaced by convection.

Thus, the micro fluid actuator 5 executes a suction stroke in which the same sucks in the ambient air through the opening 2. According to the invention, the volume of the fluid channel 3 is smaller than the stroke volume of the micro fluid actuator 5. Thus, the ambient air sucked in through the opening 2 flows through the front fluid channel portion 3a, through the portion 3c adjacent to the sensor 4 and through the rear fluid channel portion 3b into the cavity 24 of the micro fluid actuator 5. Thus, the sucked-in ambient air circumflows the sensor 4.

Subsequently, the sucked-in ambient air is ejected back out by the micro fluid actuator 5 through the opening 2. For this purpose, the micro fluid actuator 5 executes a pressure stroke in which the sucked-in air flows through the fluid channel 3 in the reverse direction and is released to the surroundings through the opening 2.

Thus, the invention solves the problem of the prior art in which a micro pump sucks in air and subsequently ejects the sucked-in air into the mobile device. Whereas, in the mobile device 1 according to the invention, the micro fluid actuator 5 sucks in a fluid volume through the fluid channel 3 and ejects the sucked-in fluid volume via this fluid channel 3. In other words, the micro fluid actuator 5 pushes a fluid volume back and forth in the fluid channel 3.

In the following, embodiments of the invention are summarized in other words.

One component of this disclosure is a flat membrane actuator which may shift an air volume (back and forth) in a cyclic manner, and to which one (or several) sensor(s) and a fluid line are connected.

The dead volume in the hose and in the fluid adapter up to the sensor is to be smaller than the (air) volume which the actuator may shift.

For example, the actuator may be driven in the following manners:
  piezo-electrically
    monomorphic bending converter
      adhered PZT ceramic
      thin layer (AlN, zinc oxide . . . )
      thick layer PZT
  electromagnetically
  electrostatically
  by electroactive polymer actuators
  thermically, e.g., by a shape memory alloy
  with the motor for the vibrating alert as a drive for the membrane, etc.

A conceivable embodiment is a piezo membrane converter 5. The same may be built in a very flat manner (precondition for mobile radio devices—design height with a carrier of less than 0.5 mm), and may still shift a large stroke volume of several mm³. See FIG. 2 with a piezo membrane actuator 5, for supplying a sensor 4 with fresh air.

Instead of a hose, a rigid tube may be used as the fluid channel 3.

All fluid connectors should be sealed so that the air from the opening 2 is sucked in. Also, several sensors 4 may be arranged (preferably in series).

A parallel arrangement makes sense when the flow resistances of all sensors 4 are approximately the same.

Also, several actuators 5 may be used, e.g., one for each sensor 4.

As appropriate, a double membrane may also be used in order to keep the voltage low.

The fluidic paths should be designed such that there are as few corners and dead rooms present as possible. In this case, it is ensured that little dispersion and carry-over occurs. In the best case, the stroke volume of the micro fluid actuator 5 just has to be as large as the dead volume (from the suction opening 2 up to the sensor 4). In reality, the stroke volume will be made larger than the dead volume by a certain factor.

An air-permeable membrane may be arranged between the suction opening 2 and the sensor 4, or between the sensor 4 and the micro fluid actuator 5 (e.g., micro pump), which does not let pass condensed liquids, e.g., a hydrophobic (e.g., teflon-coated) filter membrane having a small pore size and a large "bubble point" in order to protect the sensor 4 from liquid. According to the design, this membrane has to overcome a flow resistance. Furthermore, there may be pressure drops in the supply.

Thus, the micro fluid actuator 5 should also be able:
  to generate a certain blocking pressure,
  and also to satisfy a certain compression ratio between the stroke volume and the total dead volume (that volume of the fluid line 3, the sensor 4, the fluid adapter 5 and the actuator chamber 24).

In order to ensure this, the micro fluid actuator 5 is preferably applied by the bias method (patented by Fraunhofer EMFT) in order to minimize the dead volume of the actuator chamber 24.

Before sucking in the air sample, the membrane actuator 5 is operated (e.g., by applying a positive voltage) and moves to its lower position. Now, the dead volume is at a minimum.

Then, the actuator 5 is moved to its upper position (e.g., by switching off the voltage, or by applying an appropriate negative voltage). In doing so, a negative pressure is generated in the actuator chamber 24, ambient air is rapidly sucked in and is supplied to the sensor 4 so that measuring the air parameters may take place.

NUMERICAL EXAMPLE

Actuator 1 (diameter: 9.6 mm)
Size: 10×10×0.5 mm³,
Membrane diameter: 9.6 mm
Membrane thickness: 30 μm
Piezo thickness: 60 μm
d31: 250 m/V
Drive voltage: +90/−24 V
Resulting Stroke Data:
Stroke volume: 2.35 mm³
Blocking pressure: 14 kPa
Actuator 2 (diameter: 14.6 mm)
Size: 15×15×0.5 mm³,
Membrane diameter: 14.6 mm
Membrane thickness: 40 μm
Piezo thickness: 80 μm
d31: 250 m/V
Drive voltage: +120/−32 V
Resulting Stroke Data:
Stroke volume: 9.4 mm³
Blocking pressure: 11 kPa
Dead Volume from the Opening to the Sensor:
Hose or Tube
Length: 10 mm
Inner diameter 0.2 mm
Dead volume=$l\ r^2\ \pi$=10 mm×(0.1 mm)²×3.14=0.32 mm³
Fluid Adapter
Length: 2 mm
Inner diameter 0.2 mm
Dead volume=$l\ r^2\ \pi$=2 mm×(0.1 mm)²×3.14=0.06 mm³
Sensor Housing Length: 1.5×1.5 mm²
Height: 0.2 mm
Dead volume=0.45 mm³
Total Dead Volume
0.83 mm³

I.e., in the actuator 1, the stroke volume is larger than the dead volume by a factor of 2.8, in the actuator 2 by a factor of 11.3; fresh air reaches the sensor safely with each stroke.

If applicable, it may make sense to use thicker piezo ceramics, since, when using thin ceramics having such large lateral dimensions, the mechanical stresses in the piezo ceramics may become large, and breakage in the piezo ceramics may arise due to high tensile stresses.

Here, an embodiment would be:
Actuator 3 (diameter: 9.6 mm)
Size: 10×10×0.5 mm³,
Membrane diameter: 9.6 mm
Membrane thickness: 30 μm
Piezo thickness: 150 μm
d31: 250 m/V
Drive voltage: +225/−60 V
Resulting Stroke Data:
Stroke volume: 1.3 mm³
Blocking pressure: 29 kPa
Actuator 4 (diameter: 14.6 mm)
Size: 15×15×0.5 mm³,
Membrane diameter: 14.6 mm
Membrane thickness: 50 μm
Piezo thickness: 150 μm
d31: 250 m/V
Drive voltage: +225/−60 volts
Resulting Stroke Data:
Stroke volume: 6.3 mm³
Blocking pressure: 23 kPa The last two actuators comprise less stroke volume (however, with an appropriate design of the supply line, still enough), but the same are designed "more conservatively" with respect to mechanical stress.

With a double stroke actuator, the respective stroke volume may be doubled.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. Device comprising:
a housing with a housing opening defining a fluid connection between a fluid channel in the device and ambient air,
a sensor coupled to the fluid channel and disposed in the housing, configured to sense at least one component of the ambient air,
a micro fluid actuator arranged downstream of the sensor and disposed in the housing, configured, in the suction stroke, to suck in fluid through the fluid channel and to transport the same towards the sensor, and, in the pressure stroke, to transport the sucked-in fluid through said fluid channel back towards the housing opening,
the sensor being arranged spaced apart from the housing opening, and the volume of the fluid channel between the sensor and the housing opening being equal to or smaller than the stroke volume which the micro fluid actuator may convey with a single suction stroke,
wherein the stroke volume of the micro fluid actuator is at least 2.5 times larger than the volume of a fluid channel portion between the sensor and the housing opening, and
wherein the micro fluid actuator is a membrane actuator having a carrier and a deflectable membrane arranged at the same, and the membrane is mechanically biased so that the membrane is spaced apart from the carrier in an unoperated idle position and, upon operation, moves towards the carrier.

2. Device according to claim 1, wherein the fluid channel extends between the housing opening and the micro fluid actuator, and the fluid channel, the sensor coupled to the fluid channel, and the micro fluid actuator together form a fluid-tight arrangement which is sealed against the interior of the device.

3. Device according to claim 1, wherein the stroke volume of the micro fluid actuator is at least 10 times larger than the volume of the fluid channel portion between the sensor and the housing opening.

4. Device according to claim 1, wherein the sensor is configured to sense at least one ambient air component from the group of carbon monoxide (CO), carbon dioxide ($CO_2$), nitrogen ($N_2$), nitrous oxide ($N_2O$), volatile organic compounds (VOC), humidity and fine dust.

5. Device according to claim 1, wherein the micro fluid actuator is a membrane actuator having a deflectable membrane, and the membrane is operable in a piezoelectric or electromagnetic or electrostatic manner or by means of electroactive polymer actuators or by means of an element comprising a shape memory alloy.

6. Device according to claim 1, wherein the micro fluid actuator is a membrane actuator having a deflectable double membrane.

7. Device according to claim 1, wherein the micro fluid actuator is a membrane actuator having a carrier and a deflectable membrane arranged at the same, and the membrane including the carrier comprises a height of 0.50 mm or less.

8. Device according to claim 1, wherein the device comprises two or more sensors arranged successively in series in the flow direction.

9. Device according to claim 1, wherein the device comprises two or more sensors arranged in parallel in the flow direction.

10. Device according to claim 8, wherein the device comprises two or more micro fluid actuators, each micro fluid actuator being in fluid connection with a respective sensor.

11. Device according to claim 1, wherein an air-permeable filter element is arranged between the housing opening and the sensor, configured to collect liquid condensed in the sucked-in fluid.

12. Device according to claim 1, wherein an air-permeable filter element is arranged between the sensor and the micro fluid actuator, configured to collect liquid condensed in the sucked-in fluid.

13. Device according to claim 1, wherein the device is a mobile device.

14. Device according to claim 13, wherein the mobile device is a mobile telephone, and the housing opening provided in the mobile telephone is a microphone opening.

15. Device according to claim 13, wherein the mobile device is a mobile telephone having a vibrating alert motor, and the micro fluid actuator is a membrane actuator having a deflectable membrane, the membrane being operable by means of the vibrating alert motor.

16. Device according to claim 15, wherein the mobile device is a mobile telephone or a smartphone or a wearable or a mobile computer.

17. Device according to claim 1, wherein the device is a stationary device.

\* \* \* \* \*